United States Patent [19]

Roenker

[11] Patent Number: 5,801,810
[45] Date of Patent: Sep. 1, 1998

[54] METHOD AND APPARATUS FOR TESTING VISUAL ATTENTION CAPABILITIES OF A SUBJECT

[75] Inventor: Daniel L. Roenker, Bowling Green, Ky.

[73] Assignee: Visual Resources, Inc., Bowling Green, Ky.

[21] Appl. No.: 726,898

[22] Filed: Oct. 11, 1996

[51] Int. Cl.[6] .................................. A61B 3/00; A61B 3/02
[52] U.S. Cl. ............................................. 351/246; 351/224
[58] Field of Search ................................. 351/222, 224, 351/226

[56] References Cited

U.S. PATENT DOCUMENTS

| | | | |
|---|---|---|---|
| 4,421,392 | 12/1983 | Crick et al. | 351/224 |
| 4,429,961 | 2/1984 | Sheingorn | 351/226 |
| 4,971,434 | 11/1990 | Ball | 351/224 |
| 5,381,195 | 1/1995 | Rootzen | 351/222 |

OTHER PUBLICATIONS

K. Ball et al., "Developmental Changes in Attention and Visual Search Throughout Adulthood", *The Development of Attention: Research and Theory*, pp. 489–507, 1990.

K. Ball et al., "Clinical Visual Perimetry Underestimates Peripheral Field Problems in Older Adults", *Clin. Vision Sci.*, pp. 1–13, 1990.

C. Owsley et al., "Visual/Cognitive Correlates of Vehicle Accidents in Older Drivers", *Psychology and Aging*, pp. 403–415, 1991.

K. Ball et al., "Identifying Correlates of Accident Involvement for the Older Driver", *Human Factors*, pp. 583–595, 1991.

K. Ball et al., "The Useful Field of View Test: A New Technique for Evaluating Age-related Declines in Visual Function", *Journal of the American Optometric Association*, pp. 71–79, Jan. 1993.

C. Owsley et al., "Assessing Visual function in the Older Driver", *Medical Considerations in the Older Driver*, pp. 389–401, May 1993.

K. Ball et al., "visual Attention Problems as a Predictor of Vehicle Crashes in Older Drivers", *Investigative Ophthalmology & Visual Science*, pp. 3110–3123, Oct. 1993

C. Owsley, "Vision and Driving in the Elderly", *Optometry and Vision Science*, pp. 727–735, 1994.

"The Licensing of Older Drivers", *Transportation Research Circular*, pp. 1–32, Jul. 1994.

C. Owsley et al., "Relationship Between visual Sensitivity and Target Localization in Older Adults", *Vision Res.*, pp. 579–587, 1995.

K. Ball et al., "Evaluating the Driving Ability of Older Adults", *The Journal of Applied Gerontology*, pp. 20–38, Mar. 1994.

*Primary Examiner*—Huy Mai
*Attorney, Agent, or Firm*—Brinks Hofer Gilson & Lione

[57] ABSTRACT

A system for assessing subjects for inadequate visual attention capabilities presents a sequence of display screens to the subject on a conventional computer monitor. The display screens include a foveal target and a peripheral target, and may additionally include distractor elements around the peripheral target. The display time for the displays is varied either as a function of the responses of the subject or in a preprogrammed manner. The responses are evaluated for accuracy, and are then used to generate a measurement which is used to assess the subject for adequate visual attention capabilities.

33 Claims, 5 Drawing Sheets

METHOD AND APPARATUS FOR TESTING VISUAL ATTENTION CAPABILITIES OF A SUBJECT

This invention was made with government support under Grant 5 R44 AGO9727 awarded by the National Institute of Health. The government has certain rights in this invention.

This patent document makes reference to an appendix which includes a program listing. This listing is subject to copyright protection. The copyright owner has no objection to the facsimile reproduction by anyone of this listing, as it appears in the Patent and Trademark Office files and records, but reserves all other copyright rights whatsoever.

BACKGROUND OF THE INVENTION

This invention relates to systems and methods which allow the visual attention capabilities of a subject to be tested quickly.

Ball U.S. Pat. No. 4,971,434, assigned to the assignee of the present invention, describes an efficient and reliable method for diagnosing deficiencies in a subject's Useful Field of View (the UFOV® parameter). As described in detail in the Ball patent, a series of visual displays are presented to the subject, who is asked to identify a foveal target and in some tests to locate a peripheral target. The peripheral target is positioned at varying radial distances from the foveal target and at varying angular positions. In some displays the peripheral target is embedded in a field of distractor elements.

The UFOV® parameter is a measure of the subject's ability to locate a peripheral target while simultaneously recognizing a foveal target. As explained in the Ball patent, measurements related to the UFOV® parameter can be used in diagnosing deficiencies in a subject's visual attention capabilities.

The Ball patent discloses a number of different subtests that can be performed. One prior art approach has been to use three separate subtests, which are closely related to subtests 1, 2 and 3 described at column 9, line 17 through column 10, line 8 of the Ball patent.

With this prior approach, the first subtest presents only the foveal target at varying display times. The display time is increased when an incorrect response is made and decreased when two successive correct responses are made. Seven reversals in the adjustment direction of the display time (e.g. two successive correct responses followed by incorrect response, or an incorrect response followed by two successive correct responses) are identified, and the display times at the last five reversals are averaged to yield an average minimum display time for the subject. This average is compared to normative data and a score is assigned from 0 (no difficulty with the task) to 30 (maximum difficulty).

The second prior art subtest measures the UFOV® parameter as a function of display time. The focus of this subtest is to identify the minimum display time at which an individual demonstrates a UFOV® parameter greater than a criterion level. A display time is selected based upon the threshold duration determined in the first subtest. A sequence of displays is presented, each consisting of a foveal target and a peripheral target. The number of peripheral targets correctly located (while still correctly identifying the foveal target) is determined for each of three eccentricities, and a regression line is calculated between eccentricity and number of correct responses. Based on this regression line the point of 50% correct peripheral target localization is estimated, and is identified as the UFOV® parameter for that display time. If the UFOV® parameter is greater than a criterion level, the display time is decreased. Alternately, if the UFOV® parameter size is less than the criterion level, the display time is increased. This process is repeated until the minimum duration at which the UFOV® parameter is equal to or greater than the criterion level is determined, or until the display time reaches a predetermined minimum value. This minimum display time is then scaled by comparison to normative values to generate a score ranging from 0 (no difficulty locating peripheral targets at the fastest display time) to 30 (unable to locate any peripheral targets at the slowest display time).

A third prior art subtest is performed in a manner substantially identical to the second subtest described above, except that the peripheral targets are embedded in a field of distractors. Once again, the minimum display time is determined at which the UFOV® parameter of the subject is at or beyond a criterion level. This value is then compared to a normative value as described above in connection with the second subtest.

The normative scores for all three subtests are summed to yield a total score which may range from 0 (maximum performance) to 90 (essentially unable to perform any of the tasks at the longest display time).

This approach yields a comprehensive measure of visual attention capabilities of the subject, but it is not optimally suited for all applications. For example, the approach described above may take an excessively long time to administer for use at a department of motor vehicles or a physician's office in an assessment program of the type that divides subjects into two groups: those having adequate visual attention capabilities to pass an assessment test, and those that do not.

SUMMARY OF THE INVENTION

According to a first aspect of this invention, a method is provided for testing visual attention capabilities of a subject. According to this method a sequence of visual displays is presented to the subject for a display time, and each visual display comprises a foveal target visual element and a peripheral target visual element. The display time is varied within the sequence to generate a measurement of the accuracy of the subject in recognizing the foveal target visual element and in locating the peripheral target visual element at various display times. This measurement is then used as an assessment of visual attention capabilities of the subject.

According to another aspect of this invention, a computer readable storage device is provided comprising a computer program, and this computer program includes a means for controlling a computer to create a sequence of visual displays for presentation to a subject, each visual display comprising a respective foveal target visual element and a respective peripheral target visual element, each visual display presented for a respective display time. The program also includes a means for varying the display time for the visual display within the sequence, and a means for collecting data indicative of identification of the foveal target visual element and location of the peripheral target visual element by the subject for at least some of the visual displays. The program also includes a means for generating a measurement of visual attention capabilities of the subject in response to the data.

As described below, this invention can be implemented as a system or method which allows high speed assessment of subjects, as for example in conjunction with an application for an automotive driving license or in a physician's office.

DETAILED DESCRIPTION OF THE PRESENTLY PREFERRED EMBODIMENTS

Figure 1:
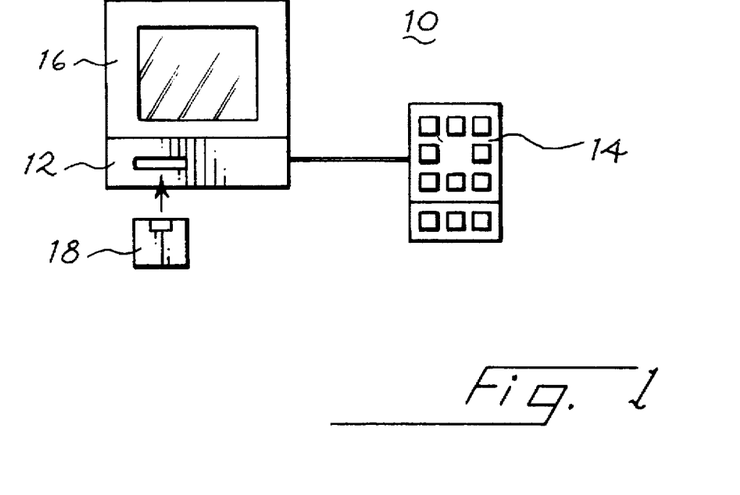
FIG. 1 is a block diagram of a computer system that can be used to implement the present invention.

Turning now to the drawings, FIG. 1 shows a computer system 10 which incorporates a presently preferred embodiment of this invention. The computer system 10 includes a conventional central processor 12 that responds to a keyboard 14 and presents visual displays on a monitor 16. The central processor 12 can read and write data on a computer-readable storage device 18.

The components 10-18 are conventional, and do not per se form part of this invention. Simply by way of example, the central processor 12 can be a conventional Pentium-based PC compatible computer, the keyboard 14 can be a conventional numeric keypad, the monitor 16 can be a conventional 12-inch CRT, and the storage device 18 can be a conventional floppy disk or a CD-ROM disc. Many other input devices may be substituted for the keyboard 14, including a joy stick, a touchscreen, a mouse, a track ball, or a voice-recognition system. As described below, some embodiments of this invention rely on manual scoring, in which case the input device may not be required.

Figure 2:
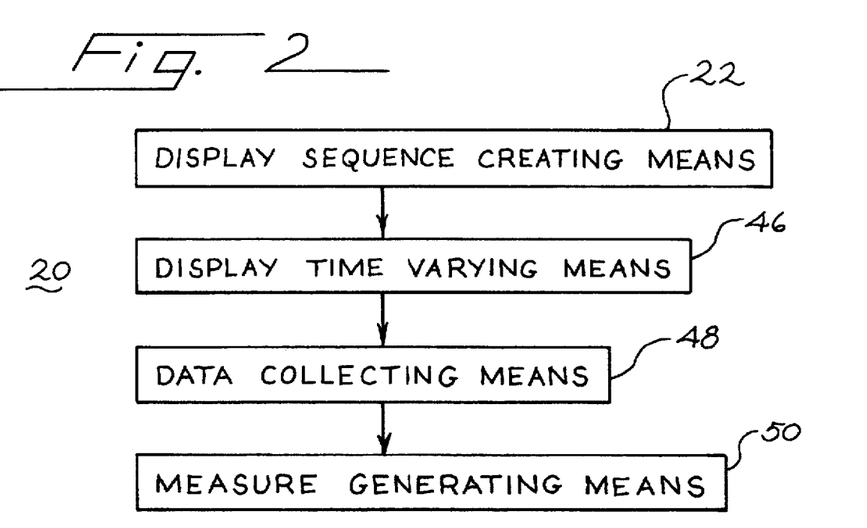
FIG. 2 is a block diagram of a computer program included in the system of FIG. 1.

As shown in FIG. 2, the computer system 10 executes a program 20 that may for example be stored on the storage device 18. The program 20 includes four basic subroutines or systems. The first of these is a display sequence creating means 22. As described below, the display sequence creating means displays a sequence of visual displays, each having a respective display time. The visual displays within any given sequence can take the forms shown in FIGS. 3, 4 and 5. For clarity of illustration, FIGS. 3-9 have been presented with a light background and a dark image. In actual practice, the background of the displayed image is preferably black, and the image, including the dark and the stippled regions of FIGS. 3-9 are bright.

Figure 3:
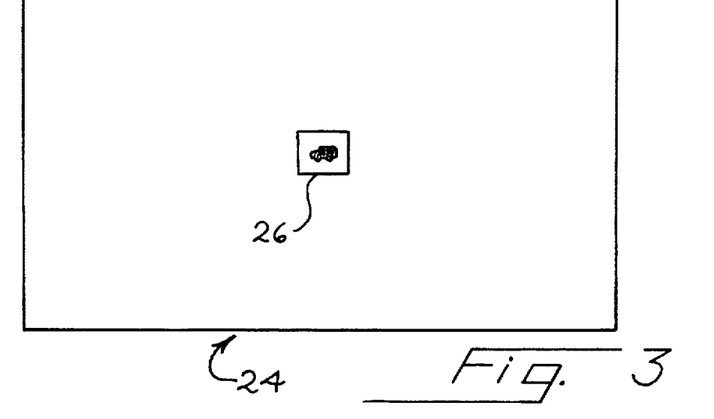
FIGS. 3, 4 and 5 are illustrative views of visual displays suitable for use in Task 1, Task 2, and Task 3, respectively, of the program of FIG. 2.

The display 24 of FIG. 3 is used for Task 1 described below, and includes a foveal target visual element 26 as the only element of the display. In actual use, the foveal target element 26 will take one of a number of visually distinct forms, and one of these forms is selected randomly, pseudo-randomly, or according to a stored list for each display 24 of the sequence.

Figure 4:
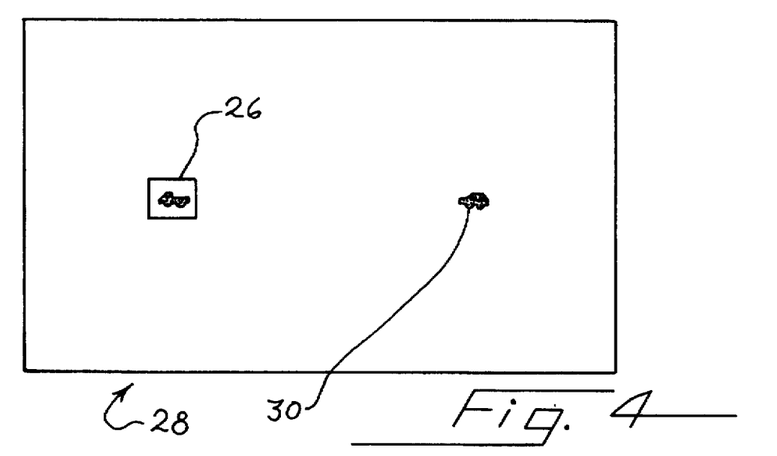

FIG. 4 shows a visual display 28 suitable for use with Task 2 described below. This visual display 28 includes a foveal target visual element 26 as described above and a peripheral target visual element 30. The peripheral target 30 can be positioned at any one or more of a number of separate visual angles (such as 10, 20 or 30 degrees with respect to the foveal target 26), and the peripheral target 30 can be positioned at any one of a number of angular positions with respect to the foveal target 26, such as those illustrated in FIG. 9. Of course, the peripheral target 30 can also take any of several different forms, depending upon the application. Within any sequence of displays the identity of the foveal target and the angular location of the peripheral target will be varied randomly, pseudo-randomly, or according to a stored list from display to display.

Figure 5:
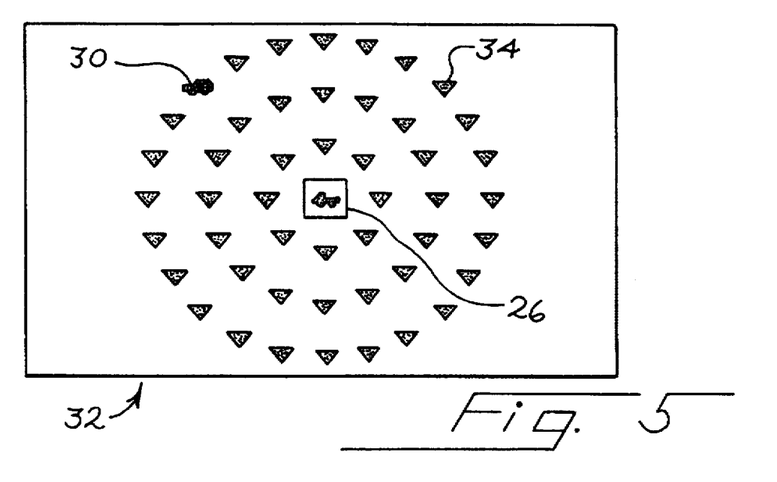

FIG. 5 shows a third visual display 32 that is suitable for Task 3 described below. The visual display 32 includes a foveal target 26 and a peripheral target 30, both as described above. As before, the targets 26, 30 are varied from display to display. Additionally, the display 32 also includes an array of distractor visual elements 34 which may take any desired form, and which may vary within a sequence. The peripheral target 30 is embedded in the distractor elements 34, which increase the difficulty of locating the peripheral target 30. As with the display 28, both the identity of the foveal target and the angular location of the peripheral target are varied within a sequence of the displays 32.

Figure 6:
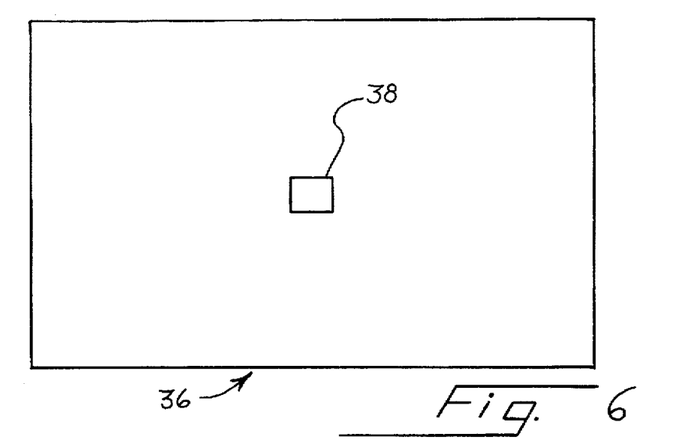
FIGS. 6, 7, 8 and 9 are schematic views of a fixation image, a mask image and first and second response images, respectively, suitable for use in the program of FIG. 2.

Preferably, when one of the displays 24, 28, 32 is displayed, it is always preceded by a fixation display 36 as shown in FIG. 6. This fixation display includes a fixation image 38 aligned with the foveal target 26 described above. The subject is asked to focus his or her vision on the fixation image 38 in order to provide a consistent starting point for viewing of the subsequent display 24, 28, 32.

Figure 7:
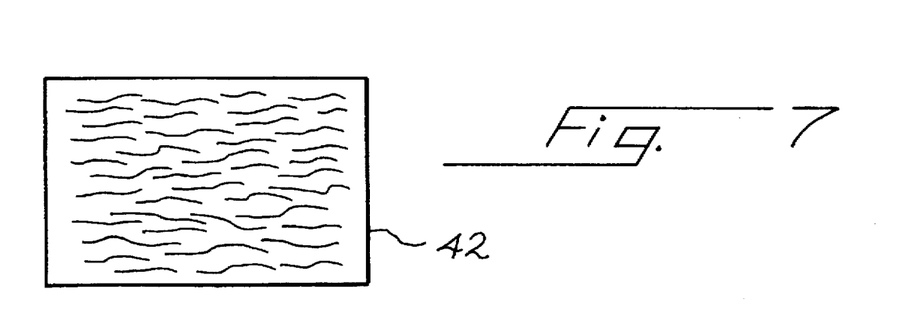

After one of the displays 24, 28, 32 has been removed, it is preferably immediately followed by a mask image 42 (FIG. 7). The purpose of the mask image is to terminate display of the image 24, 28, 32 at a repeatable time, and to eliminate any retinal after-images that might effectively prolong the display time of the preceding display 24, 28, 32.

Figure 8:
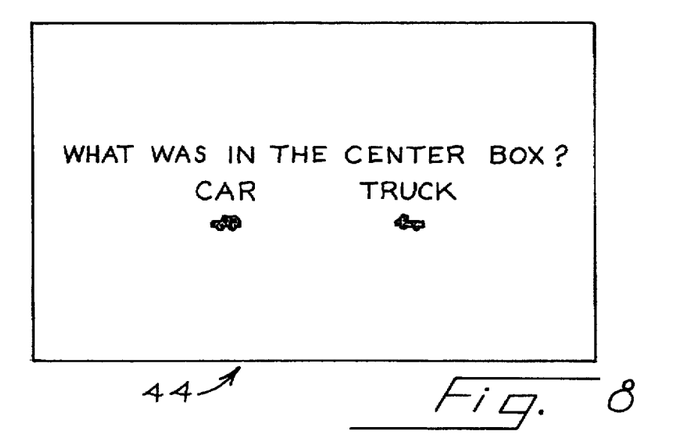
Figure 9:
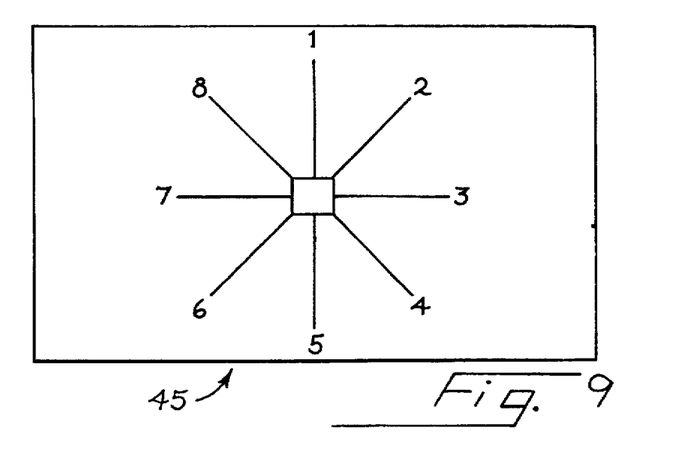

Following the mask image 42, one or more response images 44, 45 may be displayed if desired (FIGS. 8 and 9). The response image 44 may be used to prompt the subject to identify the foveal target. The response image 45 includes a number of radiating lines, for example eight lines oriented and numbered as shown. The response image 45 may be used to assist the subject in selecting the number of the line that most closely corresponds to the angular position of the peripheral target 30 on the preceding visual display 28, 32.

Returning to FIG. 2, the program 20 also includes a display time varying means which varies the display time during which the visual display 24, 28, 32 is presented within a sequence. As described in greater detail below, the display time varying means 46 can use any of several techniques for selecting the display time. The display time can for example be chosen as a function of the history of correct and incorrect responses of the subject, or the display time can be selected according to a preprogrammed sequence. Randomly selected display times are also possible in certain applications.

Once the display 24, 28, 32 has been shown for the designated display time, the program 20 then collects user responses with a data collecting means 48. For example, the subject may be asked to enter responses into the computer system 10 directly with the keyboard 14. The upper keys on the keyboard 14 can be used to select one of the eight angular positions for the peripheral target 30, and the lower keys can be used to identify the foveal target 26 as one of three alternatives. For example, the keys of a conventional numeric keypad may be marked to assist the subject in entering responses. Alternately, the subject can call out his or her responses (identification of the foveal target 26 and angular location of the peripheral target 30), and a test administrator can enter the responses via the keyboard 14.

As yet another alternative, the subject can call out his or her responses, the test administrator can record these responses in any suitable manner, and the test administrator can enter the recorded responses into the computer system 10 after all the displays have been presented. For example, the data collecting means 48 can include software for prompting the test administrator to enter the previously-recorded responses, or the previously-recorded responses can be supplied via disk or other storage medium. Other alternatives include voice recognition systems which facilitate the entry of responses either by the subject or by a test administrator. Also, the test administrator may record and assess the subject's responses, without computer assistance; in such embodiments the data collecting means can be deleted. As used herein, a user response which locates the peripheral target may specify only its approximate angular position, and a user response which identifies the foveal target may do so by selecting one of a few alternatives.

Finally, the program 20 includes a measurement generating means 50 which generates a measurement (which preferably includes a pass/fail indication), of the visual attention capabilities of the subject based on the collected data.

As described in the examples below, each sequence of visual displays generated by the means 22 preferably places all of the peripheral targets 30 at the same eccentricity, and the program 20 quickly provides a pass/fail indication after only a relatively small number of visual displays have been presented to the subject.

Figure 10:
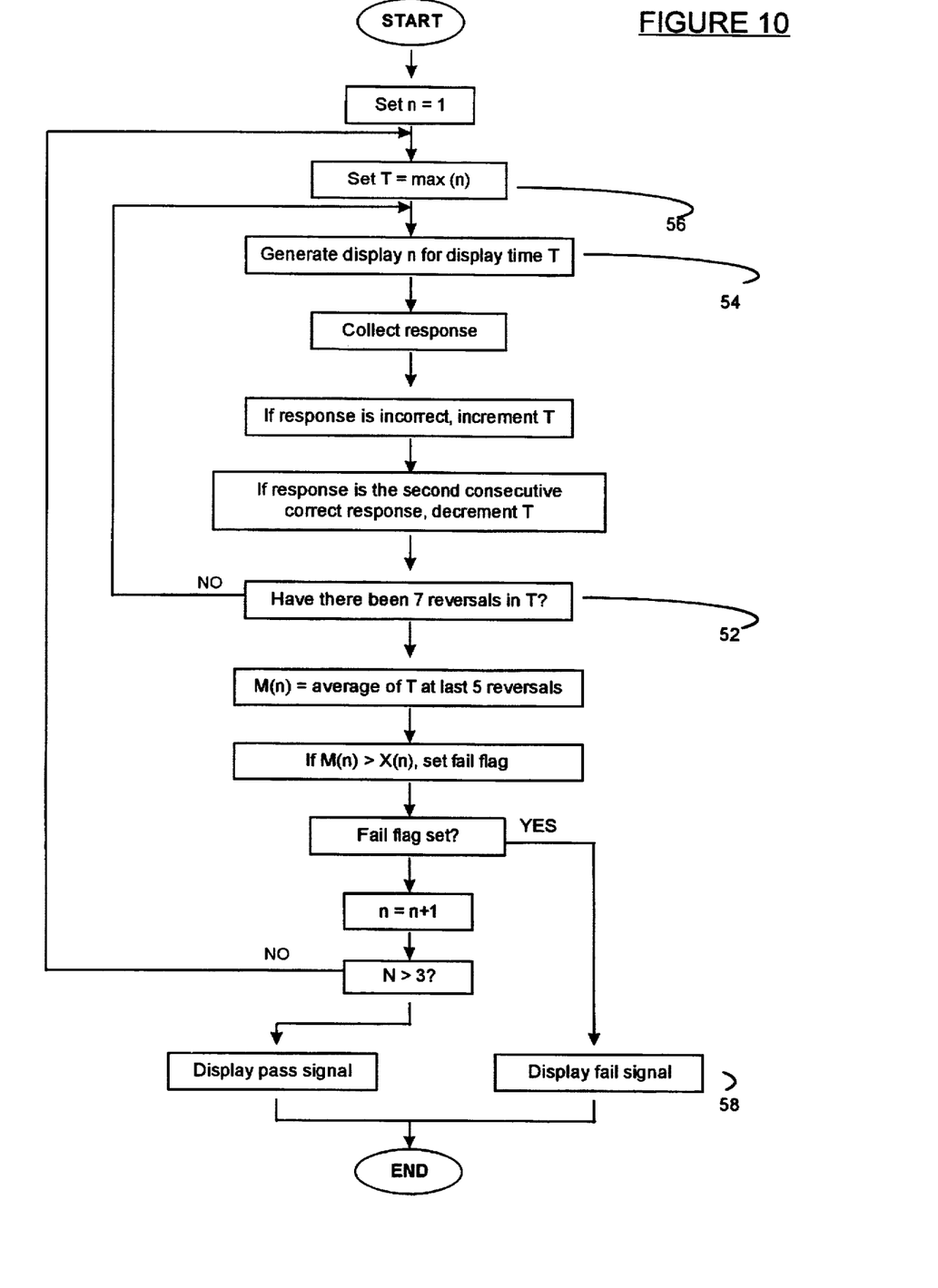
FIG. 10 is a flow chart of a first version of the program of FIG. 2.

FIG. 10 shows a flow chart of a first version of the program 20. The program of FIG. 10 uses all three display types, as shown in FIGS. 3, 4 and 5. In FIG. 10 the visual displays 24, 28, 32 are referred to as type 1, type 2, and type 3 displays, respectively.

The program of FIG. 10 initializes the parameter n to 1, sets the display type equal to the current value of n, and then sets the parameter T to the value max(n). In this embodiment T is a measure of the display time that the display will be presented. The program then generates display n for display time T. As will be described below in greater detail, the program generates up to three sequences of displays, one sequence for each of type 1, 2 and 3. During each sequence, the visual display 24 28, 32 of the respective type is shown for time T, and then the subject's response is collected. The response includes identification of the foveal target for Task 1 (display 24). For Task 2 (display 28) and Task 3 (display 32), each response includes both identification of the foveal target and location of the peripheral target. If the response is incorrect, the display time T is incremented, to provide a longer display time for the next visual display in the sequence. If the response is the second consecutive correct response, then the display time T is decremented. Preferably, the increment and decrement amounts are larger at the start of a sequence and become progressively smaller during the sequence.

The program of FIG. 10 then tests at block 52 to determine if there have been a selected number of reversals (e.g. seven) in the display time T in the current sequence. In this example, a reversal is an increment followed by a decrement or a decrement followed by an increment of T. If there have not been enough reversals of T, control is returned to block 54, and another visual display is presented in the current sequence at the current value of display time T.

This loop is repeated until there have been enough reversals of T for the current sequence. At this time the parameter M(n) is set equal to the average value of T for the last several reversals (e.g. the last five reversals). M(n) is then compared to a respective threshold value X(n). If M(n) is greater than X(n), then a fail flag is set, and control passes to block 58. Otherwise, the program then increments n by one and, as long as n is not greater than 3, control is returned to block 56. In this way, sequences of displays of types 1, 2, and 3 are presented, and M(1), M(2), and M(3) are compared to respective threshold values X(1), X(2), X(3). As explained above, if M(1) is greater than X(1) or M(2) is greater than X(2), or M(3) is greater than X(3), then the fail flag is set.

If the fail flag is set at any time, a fail signal is displayed, and the test is terminated. Otherwise a pass signal is displayed, and the test is terminated.

Alternatively, the fail flag may be set if the sum, weighted or unweighted, of M(1), M(2), and M(3) or some combination of two of the three measures is greater than some composite threshold. Furthermore, individuals may be required not to exceed the respective threshold values for one, two or all three measures M(1), M(2) and M(3) in order to pass the assessment.

Table 1 provides an example of Task 2 display time, subject response, and display time adjustment for the program of FIG. 10. In this example, the peripheral targets are all at 30 degrees of eccentricity. Any desired eccentricity can be used, but 30 degrees has been selected for this example. Also, eccentricity may be varied within a sequence of displays, if desired. The actual starting time max(2) preferably depends on M(1). In Table 1 it has been assumed that M(1) is approximately 80 milliseconds, though this could readily be varied.

TABLE 1

| Display Time T (mS) | Subject Response | Display Time Adjustment (mS) | Notes |
| --- | --- | --- | --- |
| 255 | C | 0 | |
| 255 | C | −51 | Initial adjustment is large |
| 204 | C | 0 | |
| 204 | C | −51 | |
| 153 | I* | +34 | Adjustment reduced after first reversal |
| 187 | C | 0 | |
| 187 | C* | −17 | Adjustment reduced again after second reversal |
| 170 | C | 0 | |
| 170 | C | −17 | |
| 153 | I* | +17 | |
| 170 | C | 0 | |
| 170 | I | +17 | |
| 187 | C | 0 | |
| 187 | C* | −17 | |
| 170 | I* | +17 | |
| 187 | C | 0 | |
| 187 | C* | −17 | |
| 170 | I* | +17 | |
| 187 | C | End | |

In Table 1 the subject response is identified as correct (C) or incorrect (I), and each reversal is marked with an asterisk. Note that all adjustments are in multiples of 17 milliseconds. This is a practical implementation, because the refresh rate of a 60 Hz computer monitor is one screen for every 16.67 milliseconds. In this example, the values of T at the last five reversals (153, 187, 170, 187, 170) are averaged to yield a value of M(2) equal to 173.4 milliseconds. As pointed out above, the initial increments and decrements in T are large in order to bracket the potential minimum display time quickly. Once the minimum display time has been bracketed, finer adjustments are made. As used herein, M(1), M(2), and M(3) each correspond to a measurement of visual attention capability of the subject, as does a composite measurement that includes components responsive to any one or more of M(1), M(2), M(3).

By way of example, the program of FIG. 10 can perform Task 3 in much the same manner as described above in conjunction with Table 1, except that the starting duration max(3) may be considerably slower, e.g. 357 milliseconds in the foregoing example.

By way of example, the fail flag can be set if M(1) is greater than 20 milliseconds or if M(2) is greater than 100 milliseconds. It is not required in all embodiments that all three tasks be used, and in this example the task related to M(3) is eliminated.

If desired, the program of FIG. 10 can provide a recommendation for administering further diagnostic tests, with error confidence intervals around the recommendation. The recommendation can take the following form in an assessment of automobile drivers:

Probability of low accident risk: xx %,

Probability of borderline accident risk: yy %,

Probability of high accident risk: zz %.

The specific example of FIG. 10 can readily be varied. For example, more or fewer reversals may be used, and any suitable statistical measure of the central tendency of T (including weighted averages, means, medians, modes and geometrical means) may be adopted. Also other criteria may be used to designate a reversal in T, e.g. either two consecutive correct responses or two consecutive incorrect responses.

Attached Appendix A provides a listing of a presently preferred embodiment of the program of FIG. 10. The program listed in Appendix A may be executed on an IBM PC compatible computer of the following type: 286-33 MHz processor with a VGA video card and a 13 inch VGA color monitor using a DOS operating system (e.g. a DOS shell within a Windows 3.1 environment). Of course, this embodiment can readily be adapted for other computers.

Figure 11:
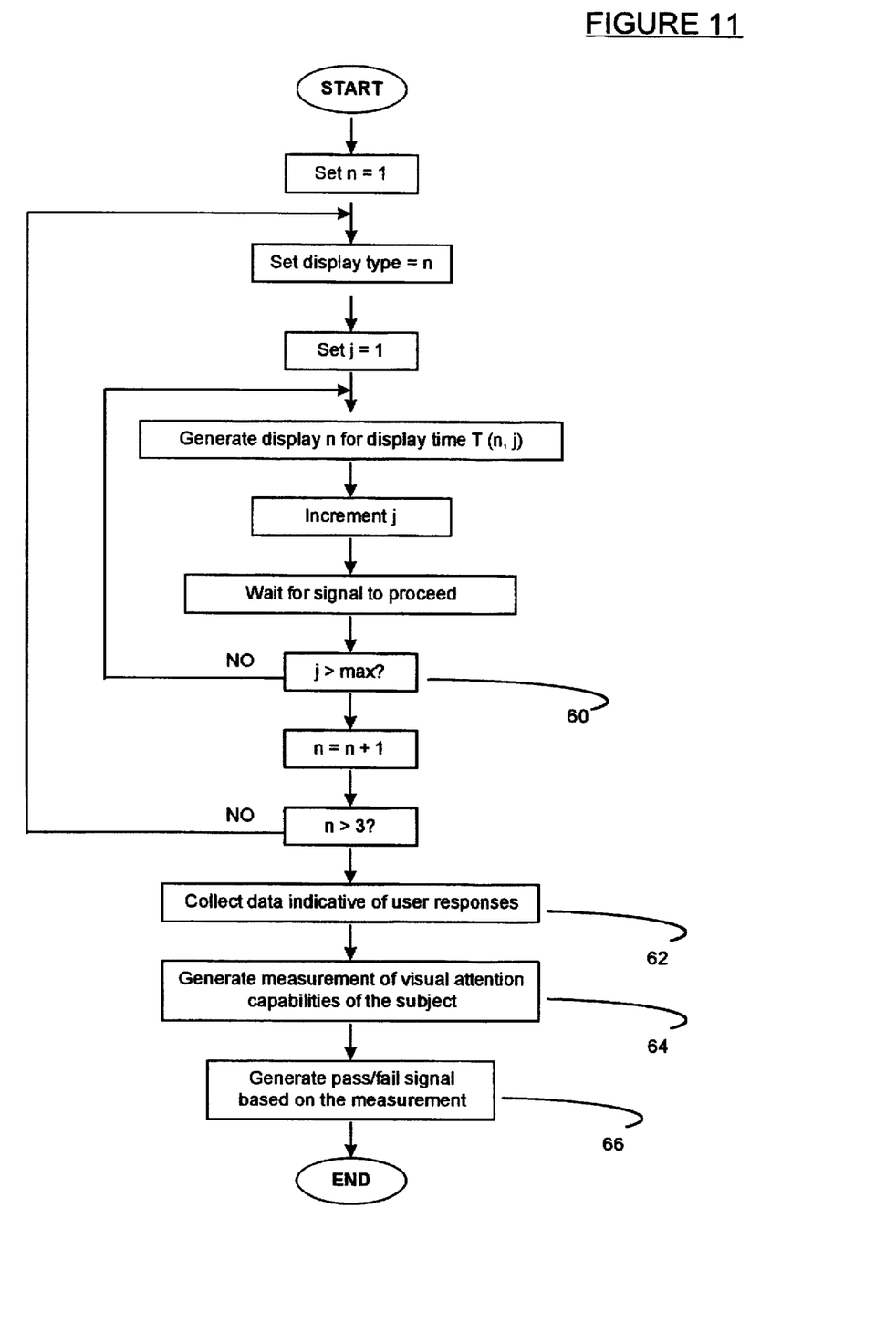
FIG. 11 is a flow chart of a second version of the program of FIG. 2.

The program of FIG. 11 represents a second embodiment of the program 20 of FIG. 2. In the program of FIG. 10 the display time T follows a preprogrammed sequence, and is not altered in response to the behavior of the subject. The preprogrammed display time T(n,j) is a matrix of values that vary both with the task number (1, 2 or 3 in this example) and the position in the sequence within a task. In the program of FIG. 11, j is initialized to 1 for all three tasks, the display of FIGS. 3, 4 or 5 is presented for display time T(n,j), and the parameter j is then incremented. Once the display has been presented, the program then waits for a signal to proceed. It is intended that in this example the subject may call out his or her responses (identification of the foveal target 26 and location of the peripheral target 30 as appropriate), and that the test administrator will then provide a signal input to the program of FIG. 11 to indicate that a response has been recorded. Alternately, a voice recognition system can be used, responsive either to the subject's responses or to a test administrator. Once the signal to proceed has been received the program of FIG. 11 then loops at block 60 until j has been incremented to the threshold value. At this point n is incremented and the sequence for the next display type is presented and the subject's responses are recorded.

The program of FIG. 11 then collects data indicative of user responses in block 62. As explained above, this can be done by the test administrator's providing the subject responses as an input in any suitable manner, or by the subject's providing responses directly. The program of FIG. 11 then generates a measurement of visual attention capabilities of the subject based on this data and generates an assessment signal such as a pass/fail signal or a scoring signal based on the measurement.

Table 2 provides an example for T(n,j), where n ranges from 1 to 3 and j ranges from 1 to 10. In Table 2 the listed values are display times T in milliseconds. Of course, Table 2 is provided only by way of example, and the selected values for T can be varied as appropriate for the particular application.

TABLE 2

| j | T for Task 1 (n = 1) | T for Task 2 (n = 2) | T for Task 3 (n = 3) |
|---|---|---|---|
| 1 | 102 | 136 | 306 |
| 2 | 68 | 102 | 255 |
| 3 | 34 | 68 | 204 |
| 4 | 17 | 34 | 153 |
| 5 | 17 | 34 | 153 |
| 6 | 34 | 68 | 204 |
| 7 | 68 | 102 | 255 |
| 8 | 68 | 102 | 255 |
| 9 | 34 | 68 | 204 |
| 10 | 17 | 34 | 153 |

The measurement of visual attention capabilities of the subject can be generated in any suitable way in block 64 of FIG. 11. For example, the program may average the values for T for all incorrect responses within the sequence or count the number of correct responses at the shortest or second shortest display time T. The measurement of block 64 is thresholded against pass/fail standards in block 66 as appropriate for the particular measurement being used.

The preferred embodiments described above provide a number of important advantages. Since eccentricity of the peripheral target is not varied within a sequence, fewer displays are needed to assess visual attention capabilities of the subject. Since the UFOV® parameter is not calculated for each display time, there is no need to present multiple displays at a constant display time. The tasks described above may be performed on a smaller computer monitor without the use of a chin rest. This results in reduced precision regarding the peripheral target eccentricity actually seen by the subject, but it reduces hardware requirements and simplifies use of the system in a setting such as a physician's office or a testing facility. The approach of FIG. 11 eliminates the need for a special mechanism such as a keyboard, joystick, touchscreen or the like, which may be needed to allow the subject to enter responses without assistance.

Of course, it will be recognized that a wide range of changes and modifications can be made to the preferred embodiments described above. For example, the particular algorithm used to develop the measurement of visual attention capability from subject responses can be varied widely, and any suitable hardware and software routines can be used to implement the methods and systems described above. In some applications, adequate assessment may be provided by Task 2 alone, by Task 3 alone, or by any combination of Task 2 or 3 and one of the remaining Tasks. The foveal target may be positioned off-center on the monitor (as long as it is aligned with the point of gaze of the subject), and the figures used for the foveal target, the peripheral target and the distractors may be varied as desired.

It is therefore intended that the foregoing detailed description be regarded as an illustration of preferred forms of the invention and not as a limitation of the invention. It is only the following claims, including all equivalents, which are intended to define the scope of this invention.

I claim:

1. A method for testing visual attention capabilities of a subject, said method comprising the following steps:
   (a) presenting a sequence of visual displays to the subject, each visual display comprising a respective foveal target visual element and a respective peripheral target visual element, each visual display presented for a respective display time;
   (b) varying the display time within the sequence;
   (c) determining a test display time based on the subjects' responses in recognizing selected characteristics of the foveal target visual elements and in locating the peripheral target visual elements in the visual displays of the sequence;
   (d) using the test display time determined in step (c) as an assessment of visual attention capabilities of the subject.

2. The method of claim 1 wherein the display time determined in step (c) is indicative of a minimum display time at which the subject recognizes the foveal target visual element and locates the peripheral target visual element.

3. The method of claim 1 wherein each visual display presented in step (a) further comprises a respective plurality of distractor visual elements, and wherein each peripheral target visual element is embedded in the respective distractor visual elements.

4. The method of claim 1 or 2 or 3 wherein the display time is varied in step (b) in response to the subject's performance in recognizing the foveal target visual element and in locating the peripheral target visual element.

5. The method of claim 1 or 2 or 3 wherein the display time is varied in step (b) in a pre-programmed sequence.

6. The method of claim 1 or 2 or 3 wherein each peripheral target visual element is positioned at a selected eccentricity and a selected angular position with respect to the respective foveal target visual element, and wherein the selected eccentricity is held constant while the angular position is varied within the sequence.

7. The method of claim 1 or 2 or 3 further comprising the steps of
   (e) presenting a second visual display to the subject for a second display time, said second visual display comprising a second foveal target visual element without any peripheral target visual elements;
   (f) repeating step (d) while progressively varying the second display time;
   (g) generating a measurement based on the subject's responses and indicative of the subject's accuracy in recognizing the second foveal target visual element at various second display times; and
   (h) using the measurement generated in step (g) as another assessment of visual attention capabilities of the subject.

8. A method for testing visual attention capabilities of a subject, said method comprising the following steps:
   (a) presenting a visual display to the subject for a display time, said visual display comprising a foveal target visual element and a peripheral target visual element;
   (b) determining whether the subject correctly recognized the foveal target visual element and whether the subject correctly located the peripheral target visual element displayed in step (a);
   (c) repeating steps (a) and (b) while varying the display time;
   (d) generating a measurement indicative of a minimum display time at which the subject recognizes the foveal target visual element and locates the peripheral target visual element;
   (e) comparing the measurement determined in step (d) against a threshold value to create an assessment of visual attention capabilities of the subject.

9. The method of claim 8 wherein said visual display presented in step (a) further comprises a plurality of distractor visual elements, and wherein the peripheral target visual element is embedded in the distractor visual elements.

10. The method of claim 8 or 9 wherein the display time is varied in step (c) in response to the subject's performance in recognizing the foveal target visual element and in locating the peripheral target visual element.

11. The method of claim 8 or 9 wherein the display time is varied in step (c) in a pre-programmed sequence.

12. The method of claim 8 or 9 wherein each peripheral target visual element is positioned at a selected eccentricity and a selected angular position with respect to the respective foveal target visual element, and wherein the selected eccentricity is held constant while the angular position is varied as step (a) is repeated.

13. The method of claim 8 or 9 further comprising the steps of
   (f) presenting a second visual display to the subject for a second display time, said second visual display comprising a second foveal target visual element without any peripheral target visual elements;
   (g) repeating step (f) while progressively varying the second display time;
   (h) generating a second measurement based on the subject's responses and indicative of the subject's accuracy in recognizing the second foveal target visual element at various second display times; and
   (i) using the second measurement generated in step (h) as another assessment of visual attention capabilities of the subject.

14. The method of claim 1 or 8 wherein at least two consecutive ones of the visual displays are characterized by a constant eccentricity of the respective peripheral target visual element with respect to the respective foveal target visual element.

15. A method for testing visual attention capabilities of a subject, said method comprising the following steps:
   (a) presenting a first sequence of first visual displays to the subject, each first visual display comprising a respective first foveal target visual element and a respective first peripheral target visual element, each first visual display presented for a respective first display time;
   (b) varying the first display time within the first sequences
   (c) generating a first measurement indicative of a first minimum display time at which the subject recognizes the first foveal target visual element and locates the first peripheral target visual element;
   (d) presenting a second sequence of second visual displays to the subject, each second visual display comprising a respective second foveal target visual element, a respective plurality of distractor visual elements, and a respective second peripheral target visual element embedded in the distractor visual elements, each second visual display presented for a respective second display time;
   (e) varying the second display time within the second sequence;
   (f) generating a second measurement indicative of a second minimum display time at which the subject recognizes the second foveal target visual element and locates the second peripheral target visual element; and (g) using the first and second measurements generated in steps (c) and (f) as assessments of visual attention capabilities of the subject.

16. The method of claim 15 wherein the first display time is varied in step (b) in response to the subject's performance in recognizing the first foveal target visual element and in locating the first peripheral target element.

17. The method of claim 15 or 16 wherein the second display time is varied in step (e) in response to the subject's performance in recognizing the second foveal target visual element and in locating the second peripheral target element.

18. The method of claim 15 wherein the first display time is varied in step (b) in a pre-programmed sequence.

19. The method of claim 15 or 18 wherein the second display time is varied in step (e) in a pre-programmed sequence.

20. The method of claim 15 wherein each first peripheral target element is positioned at a selected first eccentricity and a selected first angular position with respect to the respective first foveal target visual element, and wherein the first eccentricity is held constant while the angular position is varied within the first sequence.

21. The method of claim 15 or 20 wherein each second peripheral target element is positioned at a selected second eccentricity and a selected second angular position with respect to the respective second foveal target visual element, and wherein the second eccentricity is held constant while the angular position is varied within the second sequence.

22. The method of claim 15 further comprising the steps of:

(h) presenting a third visual display to the subject for a third display time, said third visual display comprising a third foveal target visual element without any peripheral target visual elements;

(i) repeating step (h) while varying the third display time;

(j) generating a third measurement indicative of the subject's performance in recognizing the third foveal target visual element at various third display times; and (k) using the third measurement generated in step (j) as another assessment of visual attention capabilities of the subject.

23. The method of claim 15 wherein at least two consecutive ones of the first visual displays are characterized by a constant eccentricity of the respective first peripheral target first visual element with respect to the respective first foveal target visual element.

24. The method of claim 15 wherein at least two consecutive ones of the second visual displays, are characterized by a constant eccentricity of the respective second peripheral target second visual element with respect to the respective second foveal target visual element.

25. A computer readable storage device comprising a computer program, said computer program comprising:

(a) means for controlling a computer to create a sequence of visual displays for presentation to a subject, each visual display comprising a respective foveal target visual element and a respective peripheral target visual element, each visual display presented for a respective display time;

(b) means for varying the display times for the visual displays within the sequence;

(c) means for collecting data indicative of the subject's responses in recognizing selected characteristics of the foveal target visual element and in locating the peripheral target visual element for at least some of the visual displays; and (d) means for generating a minimum display time measurement of visual attention capabilities of the subject in response to the data.

26. The invention of claim 25 wherein each visual display further comprises a plurality of distractor visual elements, and wherein each peripheral target visual element is embedded in the respective distractor visual elements.

27. The invention of claim 25 or 26 wherein the varying means varies the display times in response to the subject's performance in recognizing the foveal target visual element and in locating the peripheral target visual element.

28. The invention of claim 25 or 26 wherein the varying means varies the display times in a pre-programmed sequence.

29. The invention of claim 25 wherein, for all of the visual displays in the sequence, the peripheral target visual element is positioned at a selected eccentricity and a selected angular position with respect to the respective foveal target visual element, and wherein the selected eccentricity is held constant for all of the visual displays while the selected angular position varies from display to display.

30. The invention of claim 25 or 26 wherein the measurement is indicative of a minimum display time at which the subject recognizes the foveal target visual element and locates the peripheral target visual element.

31. The invention of claim 25 or 26 wherein the generating means generates a pass/fail signal in response to the measurement, said pass/fail signal indicative of visual attention capabilities of the subject.

32. The invention of claim 25 or 26 further comprising:

(e) means for presenting a second visual display to the subject for a second display time, said second visual display comprising a second foveal target visual element without any peripheral target visual elements;

(f) means for repeating step (e) while progressively varying the second display time; and (g) means for generating a second measurement indicative of the subject's performance in recognizing the second foveal target visual element at various second display times.

33. The invention of claim 25 wherein at least two consecutive ones of the visual displays are characterized by a constant eccentricity of the respective peripheral target visual element with respect to the respective foveal target visual element.

* * * * *